United States Patent
Chappel

(10) Patent No.: US 8,539,981 B2
(45) Date of Patent: Sep. 24, 2013

(54) PASSIVE FLUID FLOW REGULATOR

(75) Inventor: Eric Chappel, Saint-Julien-en-Genevois (FR)

(73) Assignee: Debiotech S.A., Lausanne (CH)

( * ) Notice: Subject to any disclaimer, the term of this patent is extended or adjusted under 35 U.S.C. 154(b) by 437 days.

(21) Appl. No.: 13/058,255

(22) PCT Filed: Jun. 26, 2009

(86) PCT No.: PCT/IB2009/052775
§ 371 (c)(1),
(2), (4) Date: Feb. 9, 2011

(87) PCT Pub. No.: WO2010/020891
PCT Pub. Date: Feb. 25, 2010

(65) Prior Publication Data
US 2011/0132480 A1 Jun. 9, 2011

(30) Foreign Application Priority Data
Aug. 16, 2008 (EP) .................................. 08162487

(51) Int. Cl.
*F16K 7/17* (2006.01)
(52) U.S. Cl.
USPC ............. 137/625.28; 251/61.1; 604/288.04; 604/891.1
(58) Field of Classification Search
USPC ............ 137/87.04, 510, 512.15, 517, 505.13, 137/625.28, 625.3, 859; 251/61.1, 205, 901; 604/288.04, 891.1
See application file for complete search history.

(56) References Cited

U.S. PATENT DOCUMENTS

| | | | | |
|---|---|---|---|---|
| 3,401,719 A | * | 9/1968 | Rosser | 137/493.8 |
| 3,768,508 A | * | 10/1973 | Schulte | 137/522 |
| 4,625,759 A | * | 12/1986 | Craig | 137/613 |

(Continued)

FOREIGN PATENT DOCUMENTS
DE  42 23 067  1/1994

OTHER PUBLICATIONS
International Search Report for PCT/IB2009/052775, mailed Dec. 4, 2009.

(Continued)

*Primary Examiner* — John Fox
(74) *Attorney, Agent, or Firm* — Nixon & Vanderhye P.C.

(57) ABSTRACT

A fluid flow regulator (1) of the passive type is disclosed which has a fluid inlet adapted to be connected to a fluid reservoir and a fluid outlet (13) adapted to be connected to a patient's body. The regulator comprises a rigid substrate (2) and a resilient membrane (3) tightly linked together so as to define a cavity (6) there between which is disconnected to the fluid outlet while the membrane has a first surface (12) opposite the cavity which is connected to the fluid inlet. The membrane has a plurality of through holes (15) contiguous with the cavity, to define a pathway for a fluid from the fluid inlet to the fluid outlet, and is flexible so as to be able to come into contact with the substrate as a fluid applies a sufficient pressure on the first surface. The through holes are arranged such that, when the fluid pressure increases, they close one after the other to increase the regulator fluidic resistance so that a fluid flow rate would be substantially constant as a function of the pressure applied on the first surface within a predefined pressure range.

27 Claims, 16 Drawing Sheets

(56) References Cited

U.S. PATENT DOCUMENTS

| | | | |
|---|---|---|---|
| 4,646,781 A * | 3/1987 | McIntyre et al. | 137/512.4 |
| 5,725,017 A | 3/1998 | Elsberry et al. | |
| 6,179,586 B1 | 1/2001 | Herb et al. | |
| 6,203,523 B1 | 3/2001 | Haller et al. | |
| 6,237,619 B1 * | 5/2001 | Maillefer et al. | 137/15.18 |
| 6,986,365 B2 * | 1/2006 | Henning et al. | 137/625.28 |
| 8,211,060 B2 * | 7/2012 | Steinbach | 604/141 |
| 8,276,618 B2 * | 10/2012 | Cewers | 138/37 |

OTHER PUBLICATIONS

Foreign-language Written Opinion of the International Searching Authority for PCT/IB2009/052775, mailed Dec. 4, 2009.

* cited by examiner

PASSIVE FLUID FLOW REGULATOR

This application is the U.S. national phase of International Application No. PCT/IB2009/052775 filed 26 Jun. 2009, which designated the U.S. and claims priority to Europe Application No. 08162487.6 filed 16 Aug. 2008, the entire contents of each of which are hereby incorporated by reference.

TECHNICAL FIELD

The present invention relates to a passive fluid flow regulator, more particularly of the type used in the field of drug delivery, the drug being either liquid or gaseous, for instance for pain management. The flow regulator of the present invention can also be used for draining cerebrospinal fluid (CSF) for hydrocephalus patient. The invention further relates to a fabrication process of such a fluid flow regulator as well as to a device comprising the latter.

BACKGROUND ART

Passive drug infusion devices, in contrast to active ones, do not rely on a pump to deliver a drug but rather on a pressurized drug reservoir. A known problem of these passive devices is that the drug flow rate to a delivery location, which may be a patient's body for instance, may vary as a function of the amount of drug remaining in the reservoir as far as the pressure in the reservoir depends on this amount. Such passive devices are thus usually provided with a fluid flow regulator to ensure that the drug flow rate is as constant as possible with respect to the amount of drug remaining in the reservoir.

An example of such a passive drug flow regulator is available by the Applicant under the registered name "Chronoflow" and is disclosed in U.S. Pat. No. 6,203,523 B1. This device comprises a fluid inlet adapted to be connected to a fluid reservoir and a fluid outlet adapted to be connected to a patient's body. It comprises a rigid substrate and a resilient membrane tightly linked together in peripheral linking areas so as to define a cavity therebetween. This cavity is connected to the fluid outlet while the membrane has a first surface opposite the cavity which is connected to the fluid inlet. The membrane has a central through hole contiguous with the cavity, to define a pathway for a fluid from the fluid inlet to the fluid outlet, and is flexible so as to be able to come into contact with the substrate, in case a fluid would apply a pressure on the first surface that would be larger than a first predefined threshold value. As the membrane would come into contact with the substrate in the region of its central through hole, this would occlude the latter and result in hindering a fluid from flowing through it.

This device further comprises a flow regulator open channel etched in the substrate with an inlet facing the central through hole of the membrane and an outlet connected to the outlet of the device. This channel is in the shape of a spiral curve such that, the more pressure is applied against the membrane, the more it closes the channel thus forcing the fluid to flow in it to find its way out of the cavity. Consequently, when the pressure applied on the membrane increases, the length of the fluid pathway located within the flow regulator channel increases and so does the fluidic resistance of the device. Thus, the flow rate may be kept approximately constant within a predefined range in terms of the reservoir pressure.

However, fabrication of such a device is complicated and expensive. Indeed, the substrate has to be etched according to a specific pattern which is rather delicate regarding the accuracy level that has to be respected for the flow regulation to operate properly. Thus, not only the manufacture of the substrate requires specific extra-steps, but these steps are further delicate to carry out. Depending on the dimensions of the device, specific materials such as SOI is to be used for manufacture of the substrate, which is still more expensive.

Moreover, the device manufactured through this process is then designed for one specific set of parameters regarding delivery of a drug, i.e. predefined reservoir pressure range and average flow rate.

Hydrocephalus is usually due to blockage of CSF outflow in the ventricles or in the subarachnoid space over the brain. Hydrocephalus treatment is surgical: it involves the placement of a ventricular catheter (a tube made of silastic for example) into the cerebral ventricles to bypass the flow obstruction/malfunctioning arachnoidal granulations and the draining of the excess fluid into other body cavities, from where said fluid can be resorbed.

Most of the CSF shunts have been based on the principle of maintaining a constant intracranial pressure (ICP) regardless of the flow-rate of CSF. The CSF shunts have been constructed to cut off CSF-flow when the differential pressure between the inlet and the outlet of the CSF shunt was reduced to a predestined level, called the opening pressure of the shunt.

An example of an ICP shunt is shown in U.S. Pat. No. 3,288,142 to Hakim, which is a surgical drain valve device used to control the drainage of fluid between different portions of the body of a patient, particularly for draining cerebrospinal fluid from the cerebral ventricles into the blood stream (co called ventriculo-atriostomy).

Clinical experience has proven that this principle of shunting is not an ideal solution. Sudden rises of the ICP, e.g. due to change of position, physical exercise, or pathological pressure waves result in excessive CSF drainage. Several reports in the literature (Aschoff et al., 1995) point at problems due to this overdrainage, and especially the pronounced narrowing of the ventricles has been pointed out as being the main factor leading to malfunctioning of the implanted shunting device. The reason is that the ventricular walls may collapse around the ventricular CSF shunt device, and particles (cells, debris) may intrude into the shunt device.

U.S. Pat. No. 5,192,265 to Drake et al. describes an example of a shunt seeking to overcome the above-mentioned difficulties by proposing a rather complex anti-siphoning device allowing to select transcutaneously the resistance to flow by controlling the pressure in a chamber gas-filled and being in pressure communication with one flexible wall of the main chamber where the flow is regulated.

The use of programmable valves was associated with a reduction in the risk of proximal obstruction and overall shunt revision, one possible explanation for a difference in the two populations studied is that programmable valves may allow the physician to avoid such ventricular collapse by increasing the valve pressure setting after noting clinical signs and symptoms and/or radiological evidence of overdrainage. In this way, proximal obstruction is prevented, and shunt revision surgery is avoided. One such adjustable valve is described in U.S. Pat. No. 4,551,128 to Hakim et al. However, due to the elastomeric properties of the diaphragm material, maintenance of the implanted valve may be required. Further, flow rate adjustment of this adjustable valve after implantation may require a surgical procedure.

Another adjustable valve mechanism, described in U.S. Pat. No. 4,781,673 to Watanabe, includes two parallel fluid flow passages, with each passage including a flow rate regulator and an on-off valve. Fluid flow through the passages is manually controlled by palpably actuating the on-off valves through the scalp. Although the Watanabe device permits flow rate control palpably through the scalp and thus, without surgical intervention, patient and/or physician attention to the valve settings is required.

One system, described in U.S. Pat. No. 6,126,628 to Nissels, describes a dual pathway anti-siphon and flow-control device in which both pathways function in concert. During normal flow, both the primary and secondary pathways are open. When excessive flow is detected, the primary pathway closes and flow is diverted to the high resistance secondary pathway. The secondary pathway decreases the flow rate by 90% while maintaining a drainage rate within physiological ranges, which prevents the damaging complications due to overdrainage. However, this device is intended for use with a shunt system including a valve for controlling flow rate and should be placed distal to the valve inducing cumbersome procedure due to the additional material to be implanted. The system can be used as a standalone only for low-pressure flow-control valve.

DISCLOSURE OF THE INVENTION

A first aim of the present invention is to improve the known devices and methods. More specifically, it is an aim of the present invention to propose a passive fluid flow regulator that overcomes the above-mentioned drawbacks.

Another aim of the present invention is to offset the drawback of the prior art mentioned above by proposing, as an alternative, a passive fluid flow regulator which is easier and cheaper to manufacture and which would provide more flexibility as far as its conditions of use are concerned.

To that end, embodiments of the present invention include in particular a regulator as disclosed above, wherein its membrane comprises at least one additional through hole contiguous with the cavity and arranged such that a fluid may flow through it even in case it applies a pressure on the membrane first surface that is larger than a first predefined threshold value but smaller than a second predefined threshold value. The membrane and the additional through hole are further arranged so that a fluid flow rate is substantially linear, preferably constant, as a function of the pressure applied on the membrane first surface in a range going approximately from the first to the second predefined threshold values.

According to a preferred embodiment, the membrane may comprise n additional through holes contiguous with the cavity, each j-th additional through hole being arranged such that a fluid may flow through it in case the fluid would apply a pressure on the first surface that would be larger than a j-th predefined threshold value but smaller than a (j+1)-th predefined threshold value. Again, the membrane and the n additional through holes would be further arranged so that a fluid flow rate would be substantially linear, preferably constant, as a function of the pressure applied on the first surface in a range going approximately from the first to the (n+1)-th predefined threshold values.

The through holes preferably have shapes such that they are free of any sharp edge and which could belong to the group comprising circular, elliptical, oblong and elongated shapes.

According to an alternative embodiment of the present invention, a second substrate could be affixed on the first surface side of the membrane to carry out a bi-directional fluid flow regulator.

The present invention further relates to devices comprising a fluid flow regulator as disclosed above and provides fabrication processes for such a regulator.

BRIEF DESCRIPTION OF THE DRAWINGS

Other characteristics and advantages of the present invention will become more clearly apparent on reading the following detailed description of preferred embodiments, given with reference to the appended drawings that are provided by way of non-limiting examples, and in which:

FIG. 5b shows a simplified plan view of a thin film intended to cooperate with the membrane of FIG. 5a;

MODE(S) FOR CARRYING OUT THE INVENTION

Figure 1:
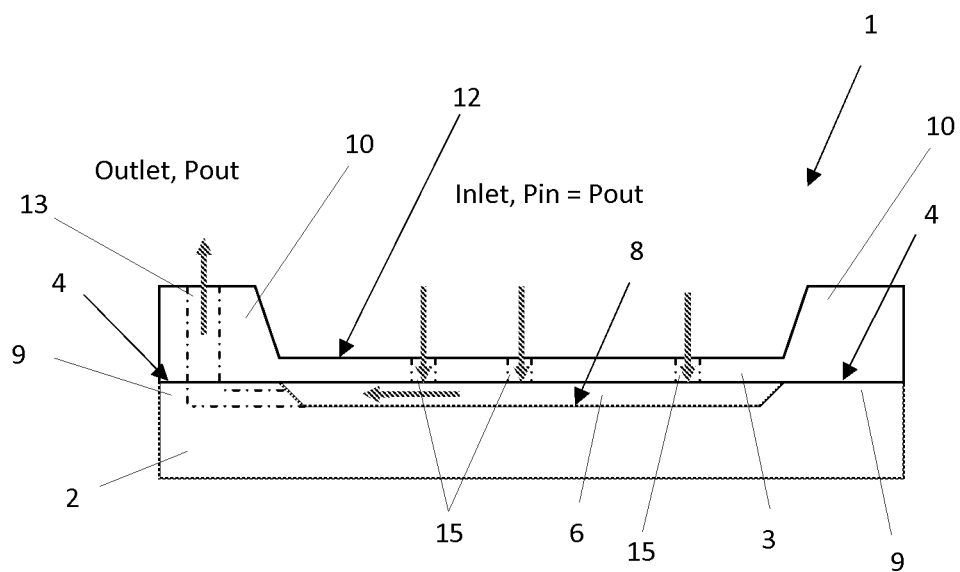
FIG. 1 shows a simplified cross-sectional view of a fluid flow regulator according to a preferred embodiment of the present invention, the regulator undergoing a first pressure value.
Figure 2:
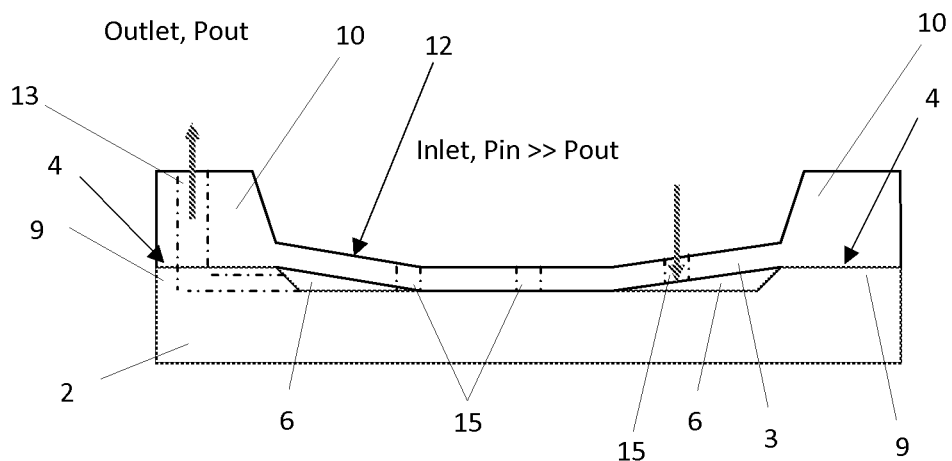
FIG. 2 shows a same view of the fluid flow regulator of FIG. 1, the regulator undergoing a second larger pressure value.

FIG. 1 and FIG. 2 show simplified cross-sectional views of a fluid flow regulator according to a first embodiment of the present invention the general behaviour of which, with respect to the pressure applied to it, is similar to that of the previously mentioned prior art device.

Indeed, the fluid flow regulator 1 shown on these drawings comprises a rigid substrate 2 and a resilient membrane 3 tightly linked together in predefined linking areas 4 so as to define a cavity 6 therebetween. The assembly of the membrane with the substrate may be carried out by direct or anodic bonding depending on the substrate material.

Typically, the linking areas 4 on both the substrate and the membrane may exhibit a roughness in the range between 0.5 and 100 nm RMS to avoid any leakage.

By way of a non-limiting example, the linking areas are located at the peripheries of both the substrate and the membrane, the substrate comprising a flat central portion 8 surrounded by an annular shoulder 9 so as to reserve a central room for defining the cavity 6 when the flat membrane is bonded to the substrate shoulder. Obviously, the shoulder may be of any other shape, for instance rectangular, without going beyond the scope of the present invention.

A shoulder 10 is also provided integral with the membrane for packaging purpose, without playing a role with respect to the implementation of the invention.

The substrate is preferably made of silicon or Pyrex (registered trademark) while the membrane is preferably made of silicon. The membrane may be linked to the substrate by any conventional bonding process.

Alternately, the substrate may also be manufactured in a plastic material, such as SAN, polycarbonate, etc., by hot embossing or injection moulding.

Typical preferred dimensions for the device are as follows: the membrane may have a thickness between approximately 50 and 150 $\mu$m while the cavity may have a height between approximately 10 and 50 $\mu$m.

The membrane 3 has a first surface 12, opposite the cavity side, which is connected to a fluid inlet on a fluid reservoir side (not shown), while the cavity is connected to a fluid outlet 13, itself intended to be connected to a patient's body for the purpose of drug delivery in this application. Of course, as will be described later in the present specification, other applications are possible with the same regulator according to the present invention.

The membrane further has several through holes 15 contiguous with the cavity so as to define a pathway for the drug to be delivered through the regulator according to the invention.

Considering conventional conditions of use of a drug delivery device as presently described, it should deliver a constant flow rate of approximately 1 ml/h of a drug having similar properties to those of water at 20° C. in a pressure range going approximately from 0 to 600 mbar.

FIG. 1 corresponds to a situation in which the pressure applied to the membrane 3 is small so that the latter is substantially flat, the respective pressures on either sides of the membrane being more or less balanced.

When the pressure applied on the first surface 12 increases, the membrane undergoes a distortion and bends towards the substrate 2 within the cavity 6, as shown in FIG. 1b.

It further appears from FIG. 2 that the through holes 15 are distributed all over the membrane so that when the latter is bent, some of the through holes may be occluded and others not, depending on the pressure.

Indeed, the Applicant has conducted experimentations, the conclusion of which being that it is possible to manufacture a membrane having a given number of through holes with a given distribution such that a pressure range may be divided in sub-ranges, each corresponding to a specific number of occluded through holes 15, and such that a fluid flow rate may be kept approximately constant within the whole range.

Thus, considering a given hole of the membrane, in case a fluid applies a pressure on the first surface 12 that is larger than a first predefined threshold value, which would result in hindering a fluid from flowing through said through hole, a next through hole may still let the fluid flow through it as long as the pressure applied on the first surface is smaller than a second predefined threshold value, and so on. When the last through hole is occluded, no fluid can flow through the device anymore, the regulator according to the invention thus playing the role of an overpressure protection system.

Advantageously, the membrane and the through holes are arranged so that a fluid flow rate would be substantially constant with respect to the pressure applied on the first surface in a range going approximately from a first predefined threshold value (corresponding to the occlusion of the most central hole) to a (n+1)-th threshold value corresponding to a n-th external through hole.

The main parameters that could drive the choice of the membrane thickness, the cavity thickness or the gap between the membrane and the substrate and the number/diameter of the through holes are the tolerances on the hole diameters as well as the tolerance on the membrane/gap thickness.

It should be noted that the regulator exhibits a great flexibility regarding the definition of the flow versus pressure profile. Indeed, the regulator may be designed such that the diagram either is substantially flat or has a slope different from zero. It may have a negative slope, for instance, without departing from the scope of the present invention.

Figure 3A:
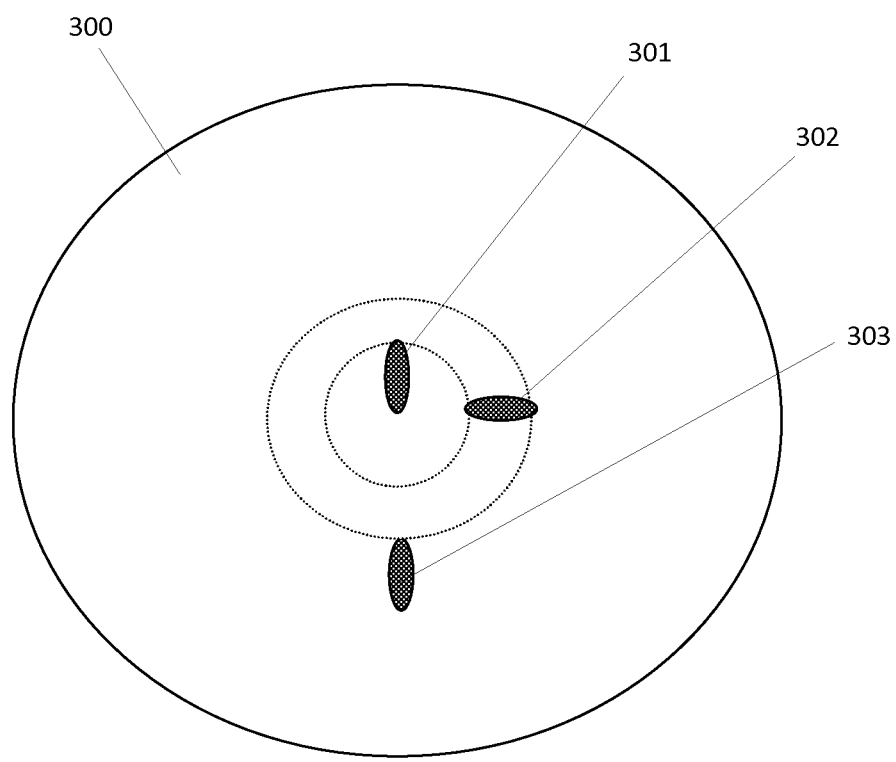
FIG. 3a shows a simplified plan view of a membrane according to a further exemplary embodiment of the present invention.
Figure 3B:
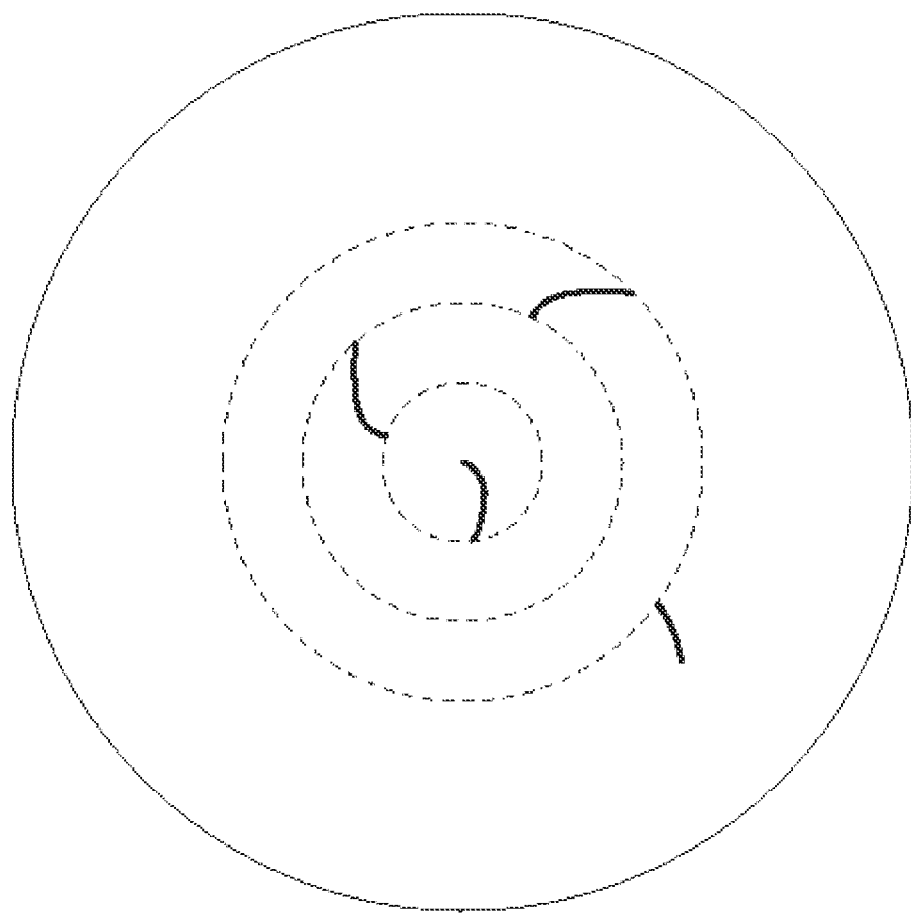
FIG. 3b shows a simplified plan view of a membrane according to a still further exemplary embodiment of the present invention.

From a general point of view, the through holes preferably have shapes such that they are free of any sharp edge to avoid stress concentration. The through hole shapes can be different from one hole to another, while the shapes may preferably belong to the group comprising circular, elliptical, oblong and elongated shapes. FIG. 3a and FIG. 3b show examples of through hole shapes and distributions in a non-limiting way.

As shown in FIG. 3a, elliptic or oblong holes may be useful for making a more continuous regulation system.

Indeed, three elliptic holes 301, 302, 303 are designed on a circular membrane 300 with their orientation not being especially radial. The holes are located so that there is a continuity in terms of fluidic resistance: the second hole 302 begins to close before or just at the same pressure necessary to completely close the first hole 301 at the centre of the membrane, and so on.

The holes may advantageously be arranged so that a spiral curve may be plotted by joining with a line the centres of the through holes.

The orientation of the holes has to be chosen as a function of the membrane deflection properties.

It is to be noted that a continuous channel, for instance in the shape of a spiral, is not recommended as far as it would deeply modify the membrane flexibility. However, specific designs may be used by a distribution of the holes made through rotation around the normal axis of the membrane, such as the exemplary design of FIG. 3b. The latter shows holes designed as sections of a spiral curve, the length of each section being chosen so as not to modify significantly the membrane flexibility.

Obviously, the narrower the holes, the more difficult they are to etch during the fabrication process. The one skilled in the art may not encounter any particular difficulty to adapt the present disclosure to design holes fitting his needs without departing from the scope of the invention.

Figure 4A:
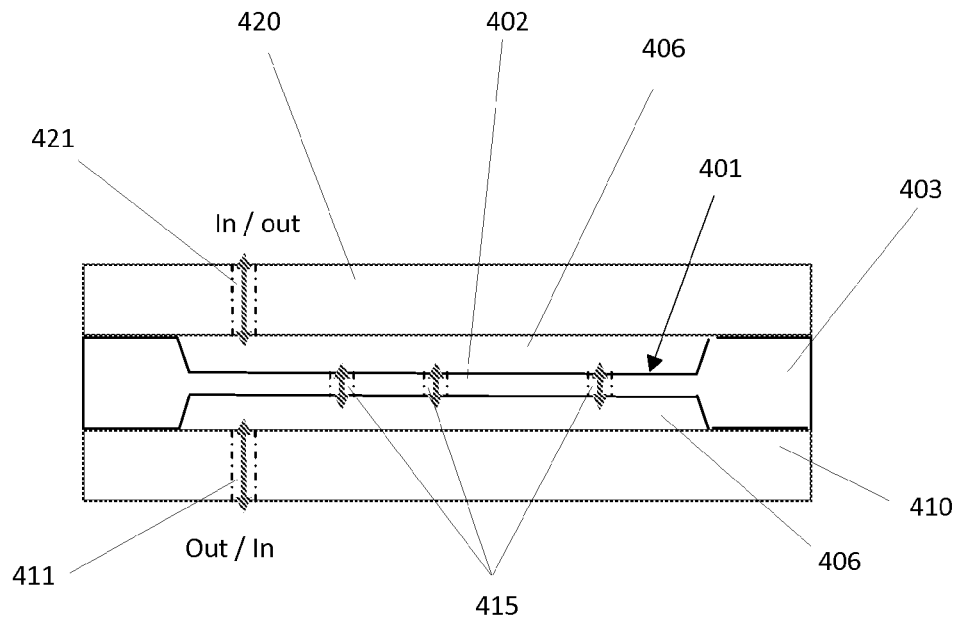
FIG. 4a shows a simplified cross-sectional view of fluid flow regulator according to a first alternate embodiment of the present invention.
Figure 4B:
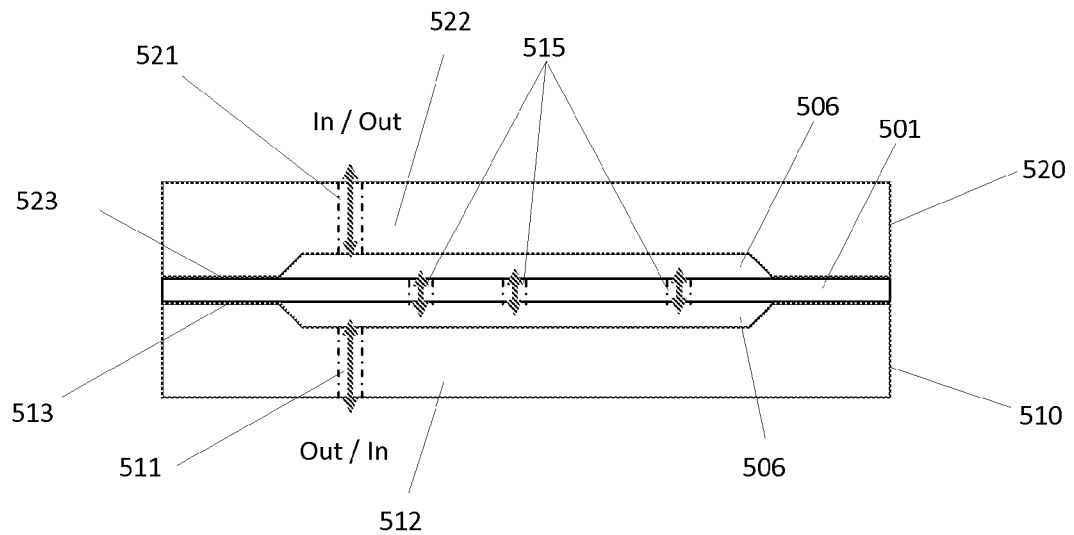
FIG. 4b shows a simplified cross-sectional view of fluid flow regulator according to a second alternate embodiment of the present invention.

FIG. 4a and FIG. 4b show two embodiments of a further implementation of the regulator according to the present invention in which it is bi-directional. Indeed, it is possible to bind a second substrate on the side of the first surface of the membrane so that the latter may deform and provide a same regulatory effect in both directions.

In FIG. 4a, the membrane 401 has a flat central portion 402 and a peripheral shoulder 403 with which a first and a second substrates 410, 420 are bound on each side of the membrane so as to define similar cavities 406 on either side of the membrane.

Each substrate has at least one hole 411, 421 to define an inlet/outlet depending on the fluid flow direction, while the membrane has a plurality of through holes 415 similar to those already described above.

In FIG. 4b, the membrane 501 is flat while each of the substrates 510, 520 has a hole 511, 521 arranged in a flat central portion 512, 522 of the substrates 510, 520 and is bound to the membrane at a peripheral shoulder 513, 523 so as to define similar cavities 506 on either side of the membrane.

Here again, the membrane has a plurality of through holes 515 similar to those already described above.

It is to be noted that the embodiment of FIG. 4b is preferred to that of FIG. 4a as far as it is easier and thus cheaper to manufacture. However, this should not be interpreted as a limitation of the present invention, its scope of protection, and equivalents are of course possible.

Regarding fabrication of the regulator according to the present invention, conventional steps may be carried out.

The substrate may be made of silicon or of Pyrex (registered trademark) while the flat central portion when there is a peripheral shoulder may be made through an isotropic wet etching step.

As already mentioned, alternately, the substrate may also be manufactured in a plastic material, such as SAN, polycarbonate, etc., by hot embossing or injection moulding.

The membrane may preferably be made of silicon regarding the particularly suitable mechanical properties of this material. The machining of the membrane may also be conducted by wet etching, while its through holes may be made using a dry etching. An anti-bonding layer on the membrane and/or the substrate may be required to prevent the sticking of the membrane onto the substrate, typically during the assembly. For a membrane in silicon and a substrate in Pyrex, a typical anti-bonding layer is silicon nitride.

Particular care should preferably be taken regarding the preparation of the different surfaces of the device, i.e. of the membrane or of the substrate, that are intended to come into contact with one another. Indeed, no unwanted particle or dust should be found on those surfaces which could compromise the operation of the device, especially in the vicinity of the through holes on the membrane. Furthermore, both the substrate and the membrane surfaces may exhibit a roughness in the range between 0.5 and 100 nm RMS to avoid any leakage between them when the membrane deforms and contacts the substrate. According to a preferred embodiment, the outlet hole of the regulator may be arranged directly in the membrane in order to simplify the fabrication process of the substrate(s).

Depending on the required thickness for the membrane, it is possible to simply bond a drilled silicon wafer onto an etched substrate. Indeed, 100 µm thick silicon wafers are conventionally available on the market and could be used directly after through holes have been etched in them.

Another fabrication process may be implemented instead of that described above, which is more flexible regarding design of the membrane, in the case of a unidirectional regulator device.

Indeed, the membrane may be designed with several holes for each finally required through hole, while a thin additional layer would cover the whole first surface of the membrane. Before using the membrane, the additional layer would then be trimmed to open the required through holes according to given specifications.

In a preferred implementation of this fabrication process, the membrane may be covered with a sacrificial layer of aluminium or silicon oxide before patterning holes in it by dry etching. It is possible to design, for instance, four holes for each finally required through hole, i.e. for each pressure sub-range. The sacrificial layer may then be covered with a thin additional layer such as a polymer layer to close all those holes. The additional layer may be applied by any adapted conventional operation such as spinning or lamination.

Next, the membrane is bound to a substrate and the through holes may be finalised empirically by applying a negative pressure in the cavity of the regulator before trimming the additional layer together with the sacrificial layer using a laser, a hot wire, a spark or so on.

Obviously, it is also possible to apply a positive pressure on the membrane first surface to finalise the through holes or to provide, alternately, that the sacrificial layer may be removed specifically before assembling the membrane with the substrate, without departing from the scope of the present invention.

The largest hole is preferably made to have a slightly smaller diameter than the nominal calculated diameter, even if the worst case in terms of diameter tolerances is considered. The next holes should have diameters gradually smaller than the first one. By applying a negative pressure in the cavity, the flow rate can be measured and the next hole that should be opened can be estimated in order to maintain approximately constant the flow rate.

Using this method, a same device can be imaged and trimmed in order to be suitable to regulate a fluid flow in a large range of flow rate values with only one general design.

Moreover, this method allows to bypass the issue of the etching accuracy, which is otherwise required, and thus to lower the device cost and dimensions.

Figure 5A:
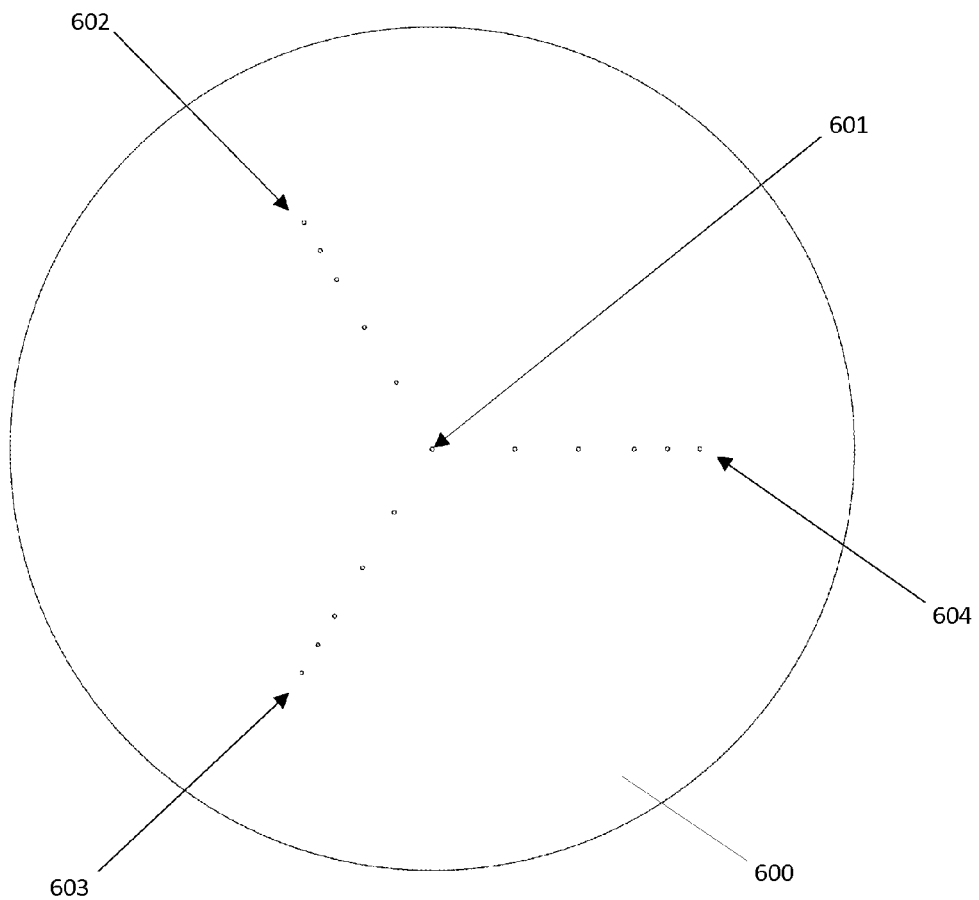
FIG. 5a shows a simplified plan view of a membrane according to a further exemplary embodiment of the present invention.
Figure 5B:
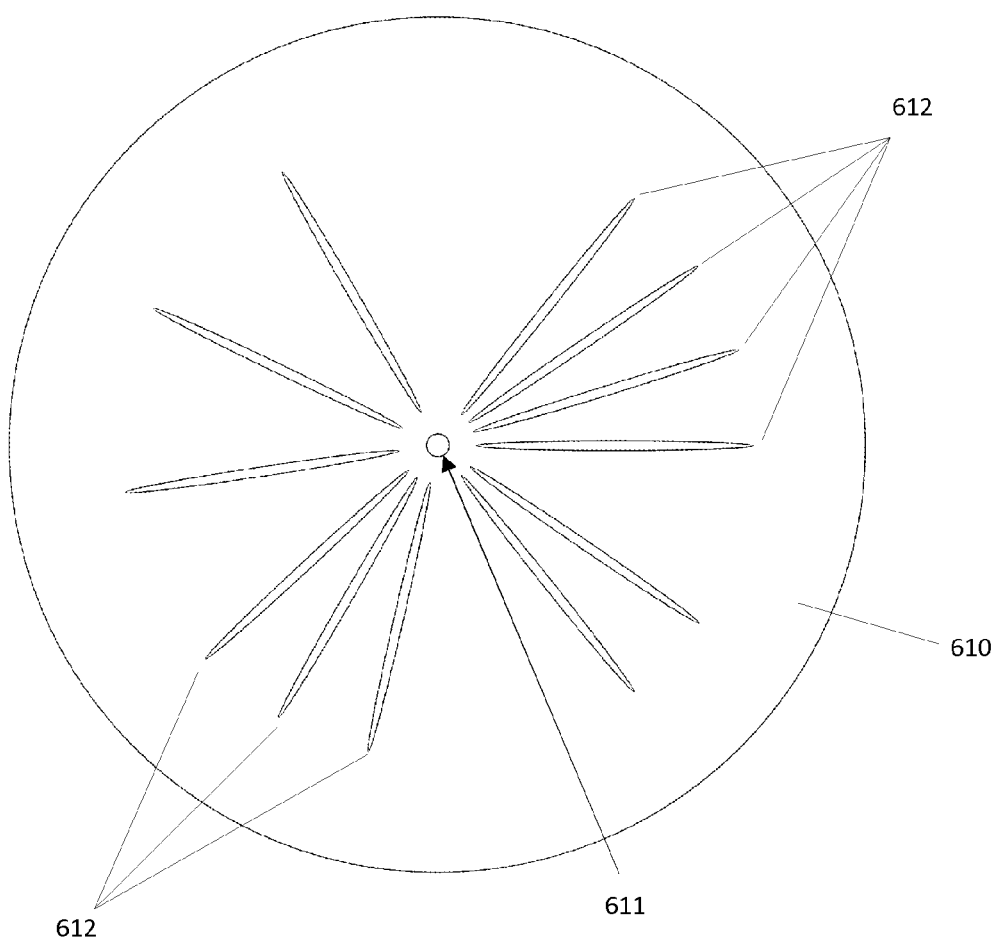
Figure 5C:
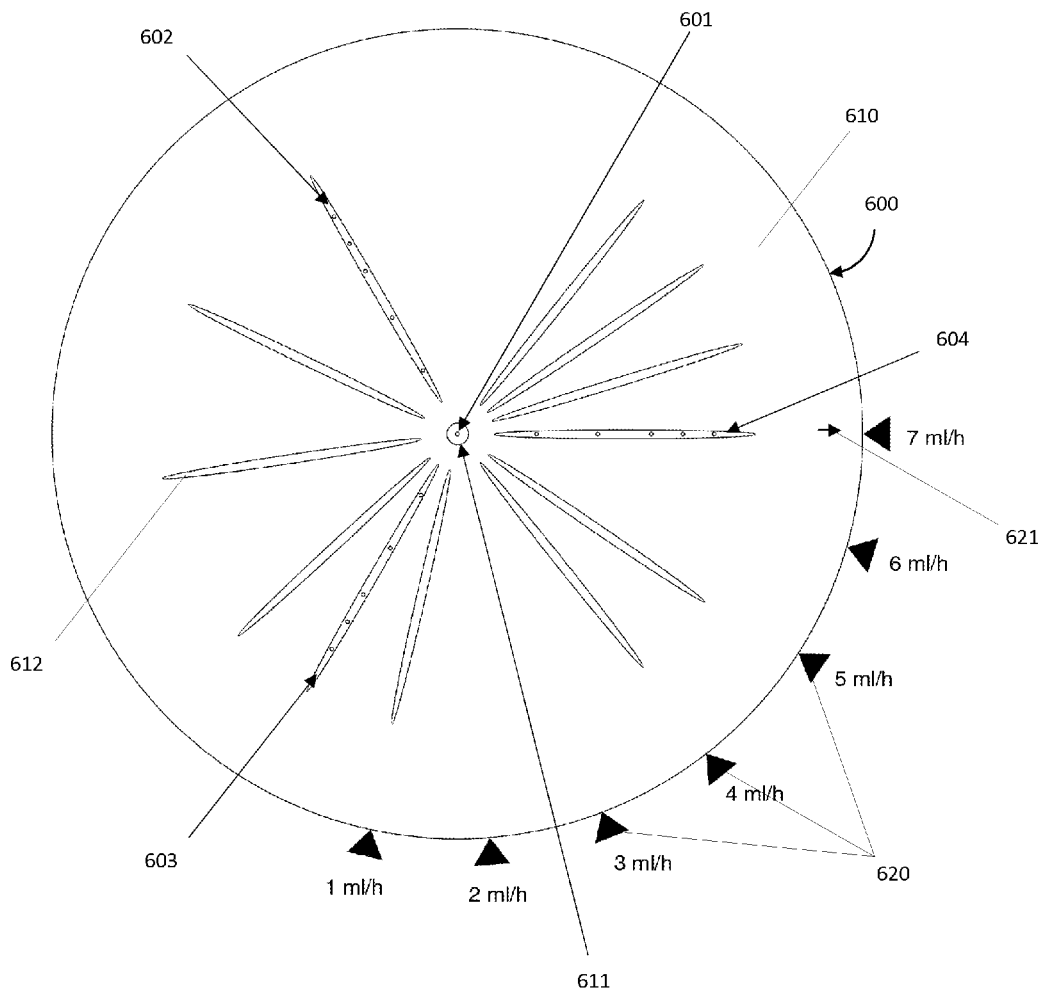
FIG. 5c shows a simplified plan view of the membrane of FIG. 5a when covered with the thin film of FIG. 5b.

FIG. 5a, FIG. 5b and FIG. 5c show simplified plan views of a further exemplary embodiment of the device according to the present invention. More precisely, FIG. 5a shows a membrane having a particular design to fit with a polymer thin film also having a particular design and illustrated on FIG. 5b, the cooperation between these two elements appearing from FIG. 5c.

On the one hand, the membrane 600 has a central hole 601 and three series of through holes 602, 603 and 604.

Each of these series includes five through holes which are here aligned on a radius of the membrane, in a non limitative illustrative manner. The three series are, for instance, regularly angularly spaced from each other, the invention being neither limited to this specific feature.

The through holes of a given series are designed such that if this series were used on its own, as described above in connection with FIG. 1 and FIG. 2, it would allow maintaining a predefined value for the fluid flow rate within a predefined pressure range. Each series is designed to correspond to its own fluid flow rate.

On the other hand, the thin film 610 illustrated on FIG. 5b is designed with a central hole 611 and a plurality of slits 612 arranged such that when the thin film is set on the membrane 600, the slits may match selectively either 0, any 1, any 2 or 3 of the through hole series 602, 603 and 604, by relative rotation between the film and the membrane, to let the corresponding series open. Indeed, the thin film should have mechanical properties such that it may be applied against the first surface of the membrane as soon as a pressure is carried out on the latter (either with a positive pressure applied from the first surface side or a negative pressure applied from the cavity side).

FIG. 5c illustrates the configuration where all three series are kept uncovered. Accordingly, if, for example, the through holes are designed such that the series 602, 603, 604 respectively correspond to fluid flow rates of 1, 2 and 4 ml/h, all the following values can be reached through suitable angular position of the thin film 610 above the membrane 600: 1 ml/h (602 is open), 2 ml/h (603), 3 ml/h (602+603), 4 ml/h (604), 5 ml/h (602+604), 6 ml/h (603+604) and 7 ml/h (602+603+604).

The device may preferably be provided with markings 620 indicating the value of the fluid flow rate as a function of the angular position of the thin film on the membrane, the thin film being also provided with a corresponding marking 621 allowing a precise relative adjustment between the film and the membrane.

The one skilled in the art may implement other embodiments based on the concept that has just been described without departing from the scope of the present invention.

Figure 6:
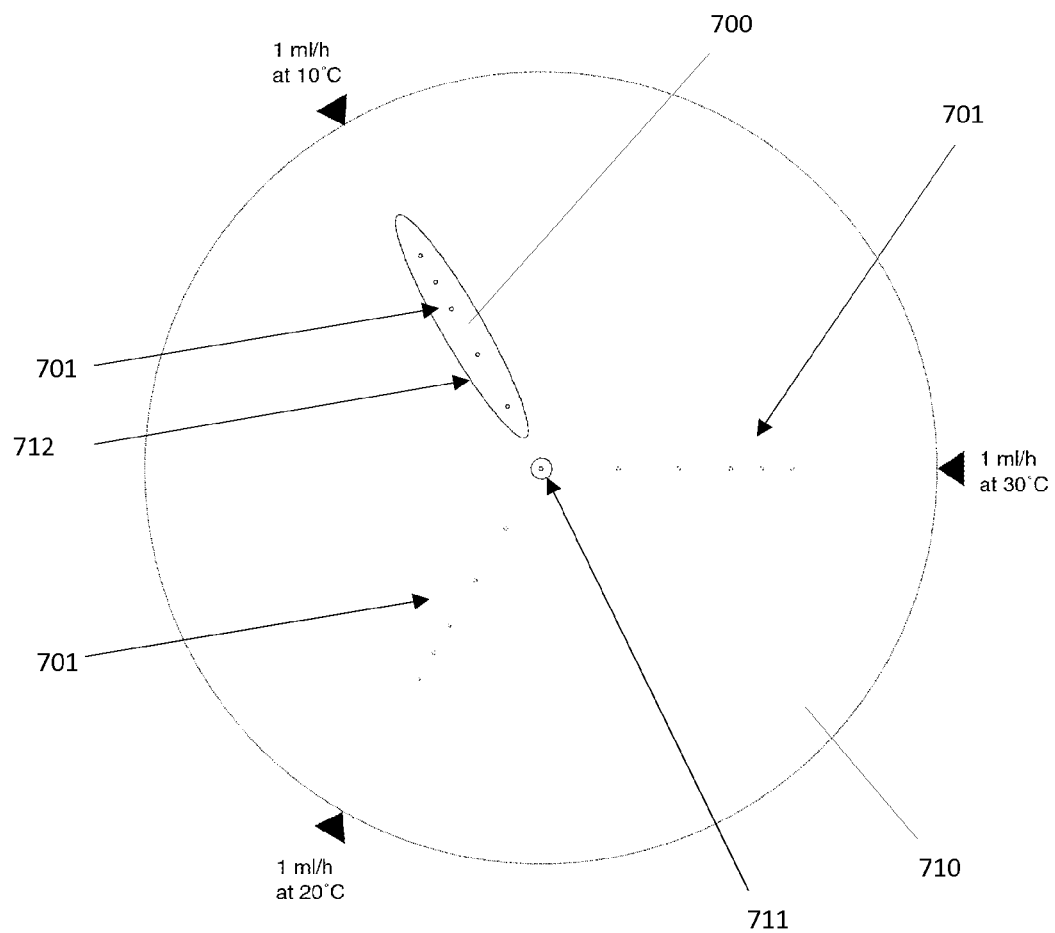
FIG. 6 shows a simplified plan view of a membrane covered with a thin film according to a further exemplary embodiment of the present invention.

FIG. 6 illustrates such a further embodiment, wherein the membrane 700 has three series of through holes 701 while a thin film 710, having a central hole 711 and a slit 712, is provided so that one single series can be kept open at any time. The through holes 701 are designed here such that each series corresponds to a predefined fluid flow rate at a predefined temperature. According to the illustrated embodiment, a first series corresponds to a fluid flow rate of 1 ml/h at a temperature of 10° C., while the other two series correspond to the same rate respectively at 20° C. and 30° C.

Obviously, it is possible to provide the membrane with further through hole series such as three corresponding to a fluid flow rate of 2 ml/h at respectively 10° C., 20° C. and 30° C., and so on, without departing from the scope of the present invention.

The device may also be used with different fluid types having different viscosities. Thus, the through hole series may be designed to take into account use of these different fluids.

The one skilled in the art may not encounter any difficulty to combine any of the embodiments that have just been described to design a device fitting his needs, such as series taking into account both viscosity and temperature for example.

The above description corresponds to preferred embodiments of the invention described by way of non-limiting example. In particular, the shapes shown and described for the various component parts of the fluid flow regulator are not limiting. For example, the numbers of through holes are not limiting. The presence of a central through hole is given as an illustrative example of an embodiment but the one skilled in the art may not encounter difficulty to design a fluid flow regulator without central through hole.

By way of example, a person skilled in the art will encounter no particular problem in adapting the present invention to his needs regarding dimensions, flow rates, materials or fabrication process steps.

Further, it should also be noted that the present device may be either applied on the skin of the patient or implanted in the patient's body, for instance in the field of hydrocephalus treatment, which typically implies a drainage conducted by means of an implanted valve.

The following description is directed more specifically to the use of the regulator for draining cerebrospinal fluid (CSF) for hydrocephalus patient as an auto-regulated valve, this description being applicable in principle to other applications as well.

Figure 7:
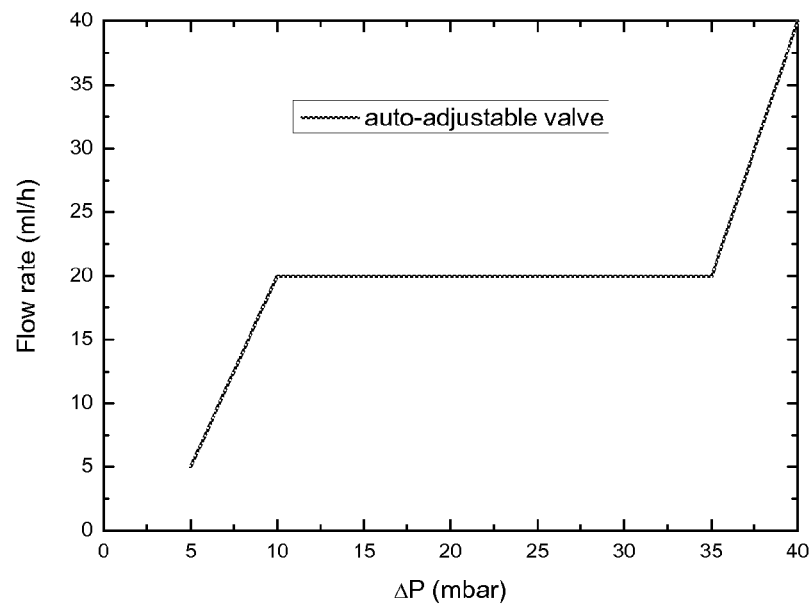
FIG. 7 illustrates a typical flow rate v. pressure characteristic for passive auto-regulated hydrocephalus valves.

FIG. 7 shows a typical flow rate versus pressure characteristic for passive auto-regulated hydrocephalus valves. The flow rate is regulated at 20 ml/h between 10 to 35 mbar. This value corresponds to the mean CSF production of 0.5 L/day. For higher CSF daily volume production, it is necessary to not regulate at high pressure in order to avoid underdrainage. This explains the shape of the curve at high pressure. At low pressure it is no longer necessary to get high flow rate (overdrainage issue). The flow rate can increase linearly from a threshold which varies from 3 to 10 mbar up to the value of 20 ml/h.

Overdrainages due to patient movement, which induces changes of the hydrostatic pressure, are strongly limited by this flow rate characteristic.

This characteristic is very close to the one of the passive flow regulator described above. At high pressure the safety shut-off system should be replaced by a standard flow restrictor. This feature can be simply obtained by shifting the last hole of the device toward the outer edge of the membrane.

Figure 8:
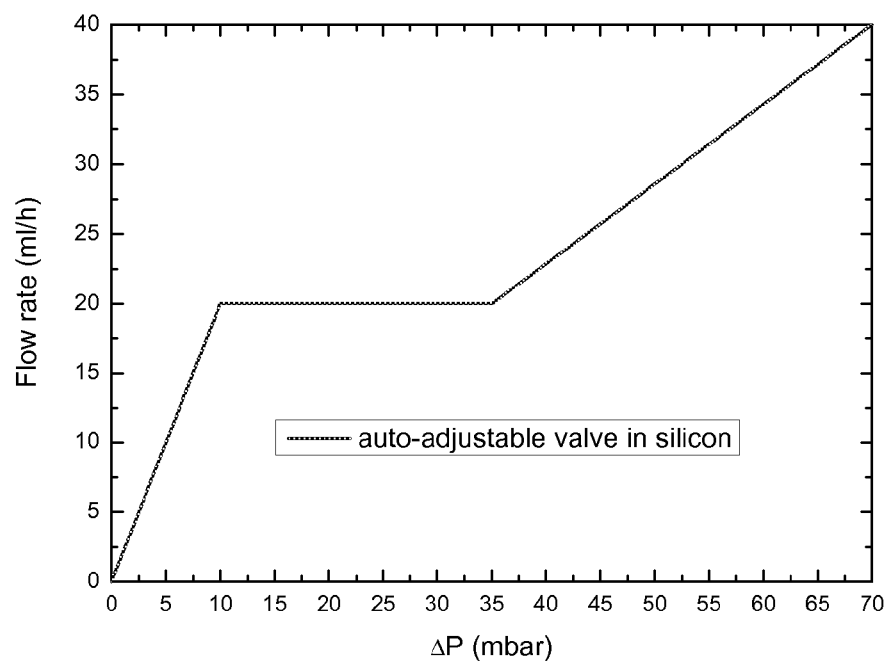
FIG. 8 illustrates the nominal characteristic of a regulator according to the present invention.

The nominal characteristic of the device according to the present invention is illustrated in FIG. 8.

The device described above in the present description is based on the elastic deformation of a membrane which goes into contact with a substrate when a pressure is applied. The flow rate is regulated via tiny holes in the membranes. FEM simulations are necessary to estimate first the shape of the membrane at the different functioning pressures.

Fluidic simulations are also necessary to estimate the fluidic behaviour at the outlet of the holes. The small dimension of the gap between the membrane and the substrate coupled to the large diameter of the membrane is indeed not favourable in terms of residual fluidic resistance. The problem has not the axial symmetry and the meshing of the tiny holes and the large fluidic pathway at their outlet is difficult.

A solution avoiding partly this effect is proposed in the disclosed embodiment. Moreover the estimation of the flow rate will become significantly easier.

The idea is simply to etch the substrate (RIE . . . ) in order to create pillars in front of the holes of the membrane. The goal is to ensure that the pressure tends quickly to the outlet pressure just after the holes. It is also important to ensure that the membrane still undergoes a symmetric deformation. The outer ring of the substrate can also be etched for a better equilibrium of the pressure at the outlet. Various masks can be designed for this etched area.

Figure 9:
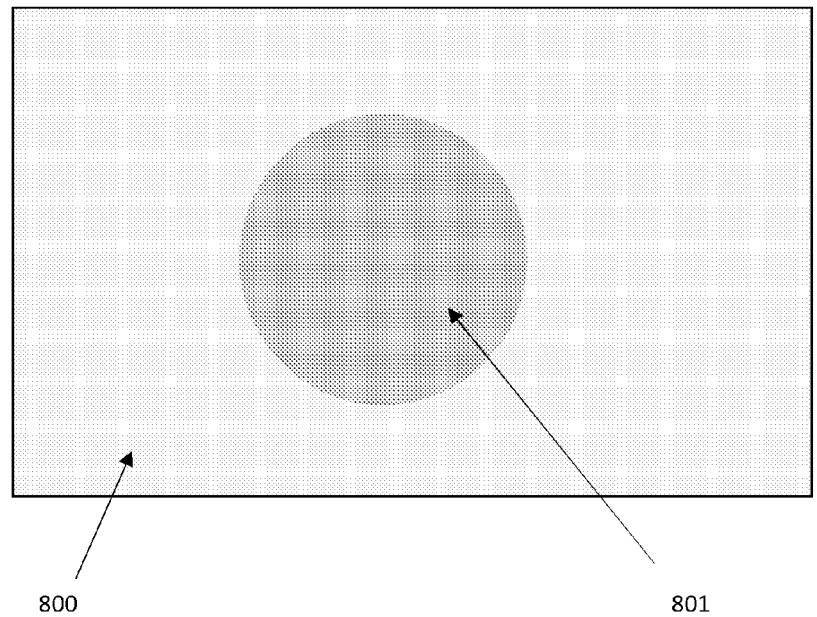
FIGS. 9 and 10 illustrate a second embodiment of a regulator according to the present invention.
Figure 10:
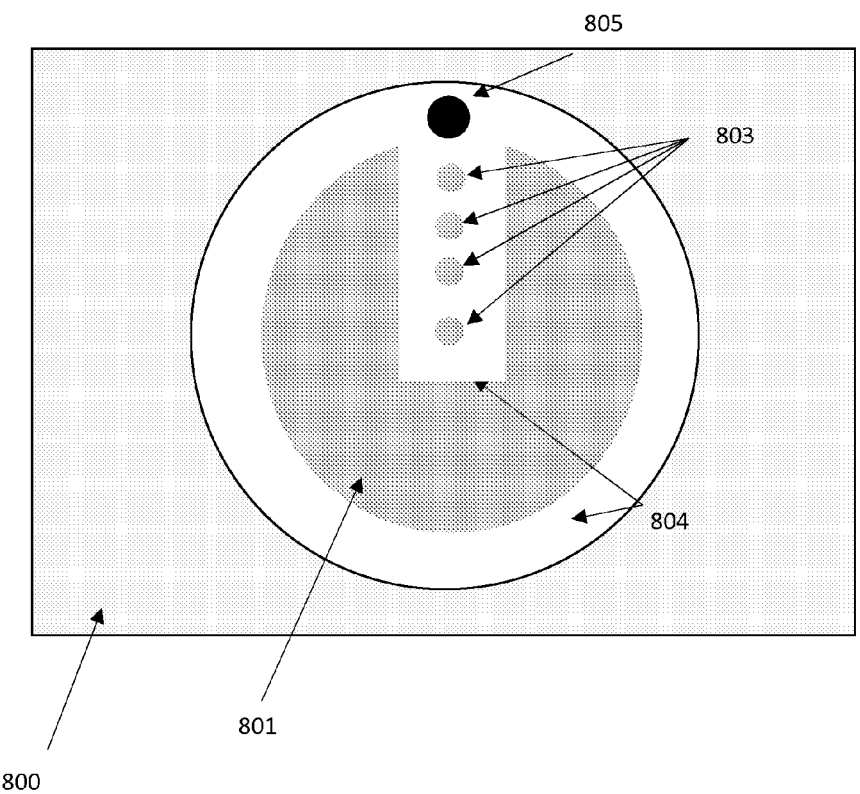
Figure 11:
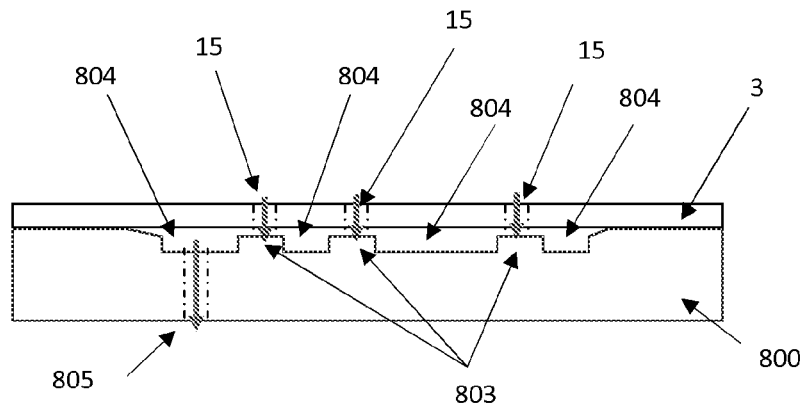
FIG. 11 illustrates a cut view of the second embodiment.

We propose below a very basic mask for the etching of the substrate (see FIGS. 9, 10 and 11): the initial flat substrate 800 is first etched over an area 801 that will define the diameter of the membrane (not represented here), typically by a wet etched of the silicon. Then an additional etch (typically a dry etch) is carried out in order to define pillars 803 and a second level of the cavity 804. The darker parts of the substrate (first etching level 801) and pillars 803 form the support for the membrane when a pressure is applied. The outlet of the valve is referenced 805. A schematic cut-view of the system is illustrated in FIG. 11 showing the pillars 803 and the levels of etching 804 and the membrane 3 with the holes 15.

The substrate could be Pyrex, silicon or plastic. For Pyrex or Si an anti-bonding layer is needed to prevent the sticking of the membrane onto the pillars during the assembly.

At a 100 μm thickness, a 200 mm wafer can no longer support itself (150 μm for 300 mm wafers). It is also necessary to use a substrate for handling concern, which can be removed after the anodic bonding.

In order to be sensitive to low pressures it is necessary to use a thin membrane and/or a small gap between the membrane and the substrate and/or a large membrane diameter. Typical membrane shunts are quite large, about 35 mm or more in diameter.

Max membrane diameter=15 mm

Membrane thickness t fixed at t=50 microns.

A contact pressure of 10 mbar leads to a gap between the membrane and the substrate of 25 microns.

The flow can be modelled using simply fluidic resistances in series including the holes and the opening between the pillars and the membrane.

Fluidic resistance $Rf_i$ of the holes, diameter $D_i$, dynamic viscosity of the liquid $\eta$ (SI units):

$$Rf_i = \frac{128\eta t}{\pi D_i^4}$$

Fluidic resistance $Rf_i'(P)$ of the opening, with $h_i(P)$ is the distance between the membrane and the pillar at the pressure P for the pillar and the hole I, and $D_i'$ is the pillar diameter:

$$Rf_i'(P) = \frac{6\eta}{\pi h_i(P)^3} \ln\left(\frac{D_i'}{D_i}\right)$$

The flow rate Q takes the form:

$$Q = \sum_i Q_i = \Delta P \sum_i \frac{1}{Rf_i + Rf_i'(P)}$$

The functions $h_i(P)$ are estimated using the FEM model for the membrane deformation under pressure.

The theoretical flow rate is matched using only 3 holes: the hole and pillar diameters are estimated using simulation. The numbers of holes may be varied if the alignment tolerances are too tight between the holes and the pillars. The hole located at the outer side of the membrane has no pillar.

| Parameters: | |
|---|---|
| membrane Si | Thickness 50 microns |
| E = 156 Gpa | Gap 25 microns |
| nu = 0.262 | Diameter 15 mm |

| Radial position from center (mm) | Hole diameter (um) | Pillar diameter (um) |
|---|---|---|
| 3.46 | 48 | 60 |
| 5 | 52 | 90 |
| 6.5 | 35 | 70 |

Figure 12:
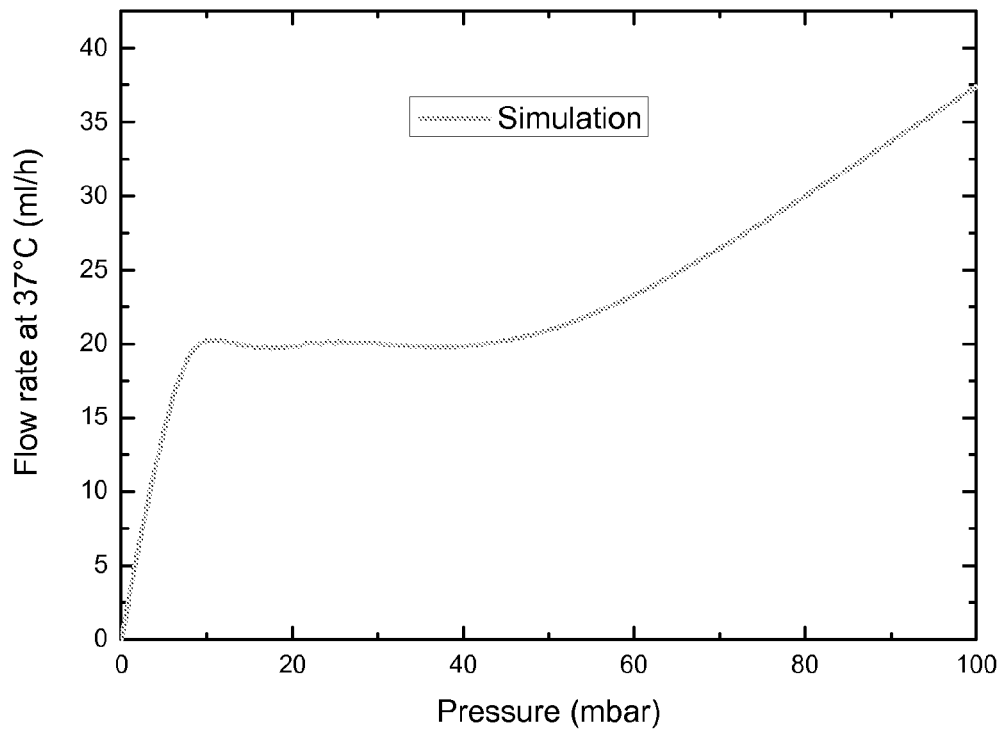
FIG. 12 illustrates the simulation characteristic of the second embodiment.

FIG. 12 illustrates a typical Flow rate v. Pressure simulation curve obtained for hydrocephalus.

Another example of realization is the following with seven holes and pillars in the drug delivery application.

Membrane in silicon

Diameter 5 mm

Thickness 50 microns

Gap 25 microns

Characteristics of the 7 holes and pillars:

| Radius (mm) | hole diameter (um) | pillar diameter (um) |
|---|---|---|
| 3 | 10 | 100 |
| 3.125 | 10 | 50 |
| 3.25 | 7 | 40 |
| 3.375 | 8 | 20 |
| 3.5 | 7 | 20 |
| 3.75 | 6 | 30 |
| 4 | 9.9 | 35 |

Figure 13:
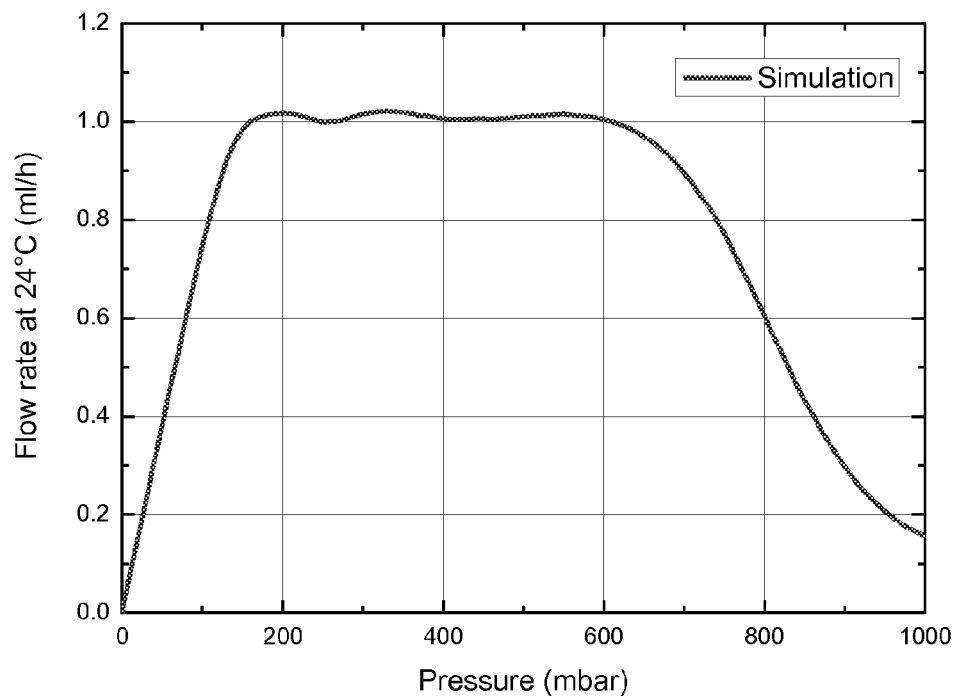
FIG. 13 illustrates the simulation characteristic of another embodiment.

FIG. 13 illustrates the Flow rate v. Pressure stimulation curve obtained with this realisation for drug delivery application.

As described above, the system can regulate the flow in both directions by placing another substrate on the front side of the membrane.

The substrate with pillars according to the principle described here above can be also used for bi-directional regulation. For the hydrocephalus treatment, since the back-flow is not allowed (risk of contamination of the ventricles), a simple check-valve is needed.

Figure 14:
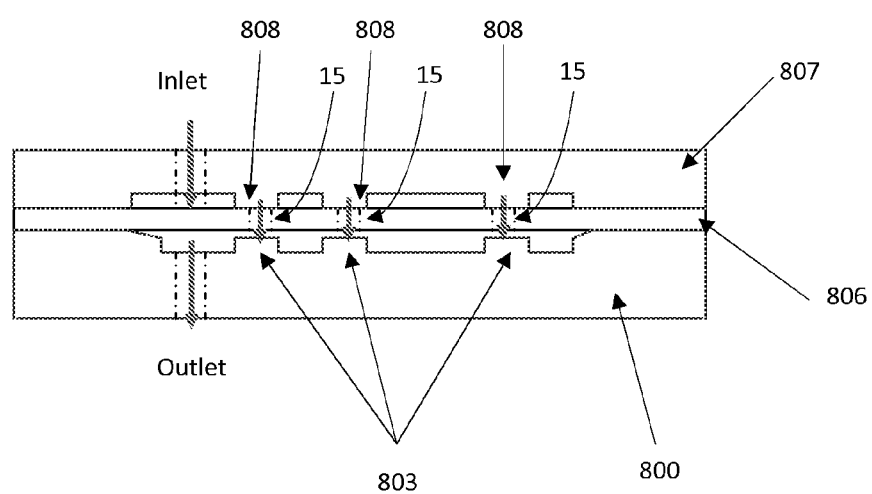
FIG. 14 illustrates a variant of the second embodiment.

In that case the simplest way to create this check valve is to put the same substrate with pillars 808 in front of the holes 15 (front side of the membrane 806) but without gap (see FIG. 14). The new pillars 808 will change the fluidic behaviour of the system and it is necessary adapt the model described previously for the simulations of the fluidic behaviour.

It is also possible to create a small pretension to the membrane, typically by adding a layer (preferably an anti-bonding layer) onto the pillars 808 of the top substrate or directly on the membrane 806 which will be also pre-stressed. This embodiment is illustrated schematically in FIG. 14 in which the parts described in relation to FIG. 11 have the same reference numbers. One clearly sees in front of the pillars 803 (on the other side of the membrane 806) the new pillars 808 of the cover 807.

In a further embodiment of the invention, it is useful to know the intracranial pressure of the patient in order to check the efficiency of the therapy and the good functioning of the device. The pressure can be monitored by a physician using a wireless system.

The pressure sensor itself could be simply made of strain gauges implanted directly in the silicon membrane that undergoes large stresses due to the CSF pressure. This is a differential pressure sensor.

A preliminary estimation of the pressure sensor sensitivity is given below. Hypothesis: the electrical insulation of the bridge will be made of an additional implanted layer of which polarity is opposite to the resistor polarity, in order to not introduce an additional physical layer (simplification of the process and better long term stability).

Simulations have been made for the estimation of the suitable implantation doses.

Substrate: silicon SC type n

Wafer (100)

Resistivity: 3 to 5 ohm·cm

Orientation of the p resistors along [110] direction

Figure 15:
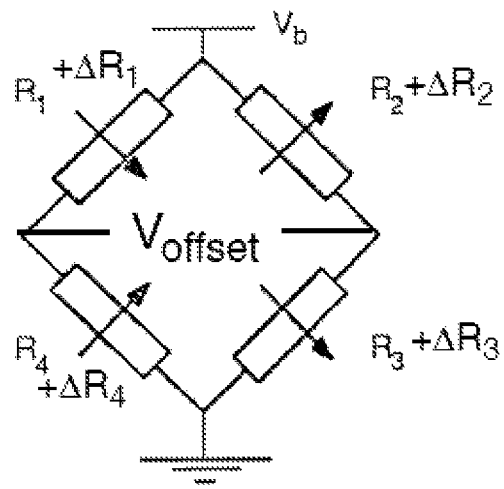
FIG. 15 illustrates a configuration of a pressure sensor.

A full bridge configuration is illustrated in FIG. 15. For matched resistors $R_1 = \ldots = R_4 = R$ we obtain:

$$\frac{V_{out}}{V_{in}} = \frac{\Delta R_1 - \Delta R_2 + \Delta R_3 - \Delta R_4}{4R} + o\left(\frac{\Delta R}{R}\right)$$

Figure 16:
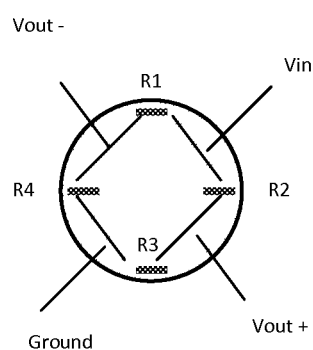
FIG. 16 illustrates another configuration of pressure sensor.

An example of orientation of the resistors R1-R4 is illustrated in FIG. 16.

According to this orientation and the symmetry of the system we have:

$$\Delta R_1 = \Delta R_3 = -\Delta R_2 = -\Delta R_4 = \Delta R$$

And finally:

$$\frac{V_{out}}{V_{in}} \approx \frac{\Delta R}{R}$$

The piezoresistive effect takes the following form:

$$\Delta R/R = \Pi_l \sigma_l + \Pi_t \sigma_t$$

With
$\Pi_l$, $\Pi_t$: longitudinal, transverse piezoresistance coefficient
and $\sigma_l$, $\sigma_t$: stress along resistor and perpendicular (in-plane) to it On silicon (100) wafers, piezoresistance effect is orientation dependent:

$$\Pi_l = \pi_{11} - \sin^2(2\theta)(\pi_{11} - \pi_{12} - \pi_{44})/2$$

$$\Pi_t = \pi_{12} + \sin^2(2\theta)(\pi_{11} - \pi_{12} - \pi_{44})/2$$

With
$\theta$=orientation of resistors with respect to [100] direction
$\pi_{11}$, $\pi_{12}$ and $\pi_{44}$: piezoresistance coefficients
n-Si: $\pi_{11}$=−102.2, $\pi_{12}$=53.4, $\pi_{44}$=−13.6($\times 10^{-11}$ Pa$^{-1}$, all)
p-Si: $\pi_{11}$=6.6, $\pi_{12}$=−1.1, $\pi_{44}$=138.1($\times 10^{-11}$ Pa$^{-1}$, all)
(at $\rho_{n-Si}$=11.7 Ωcm and $\rho_{p-Si}$=7.8 Ωcm)
We obtain:

$$\frac{\Delta R}{R} \approx \frac{\pi_{44}}{2}(\sigma_l - \sigma_t) = 69.10^{-11}(\sigma_l - \sigma_t)$$

By applying positive pressures below the membrane the signal $$\frac{V_{out}}{V_{in}} \approx \frac{\Delta R}{R}$$

is positive. In our case the pressure is applied on the top surface of the membrane (resistor side) and we should reverse the polarity of $V_{out+}$ and $V_{out-}$ in order to get a signal positive for positive pressures.

The stress is estimated in the membrane at different pressures. A non-linear model for the deflection of the membrane is needed since we have large deflections (without the substrate the free deflection of the membrane is larger than 0.4 time its thickness).

Figure 17:
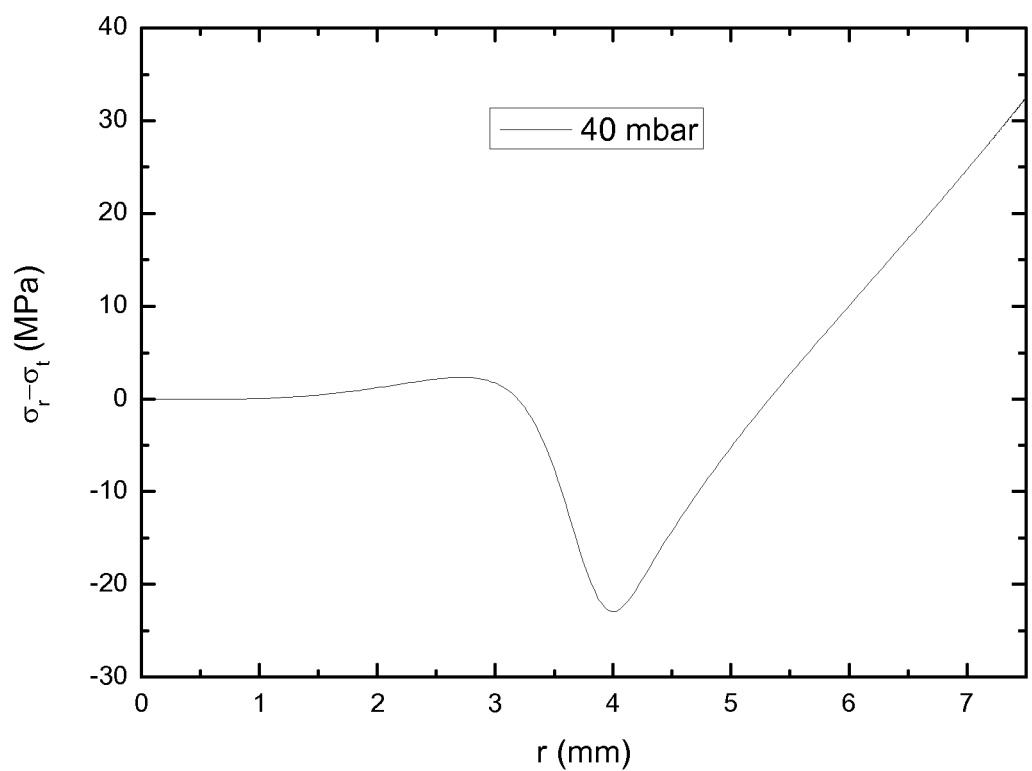
FIG. 17 shows an estimation of the bending stress of the membrane.

FEM simulations show that non-linear effects can be neglected (membrane stress) and therefore we can directly estimate the bending stress at the top membrane surface as a function of the radial position at 40 mbar as illustrated in FIG. 17. Thanks to the large membrane diameter and thickness we can neglect the stress variation in the resistor.

Close to the edge of the membrane, at 40 mbar, we have $$\sigma_l - \sigma_t \approx 30 \text{ MPa}$$

$$\frac{\Delta R}{R} \approx 0.0207$$

Figure 18:
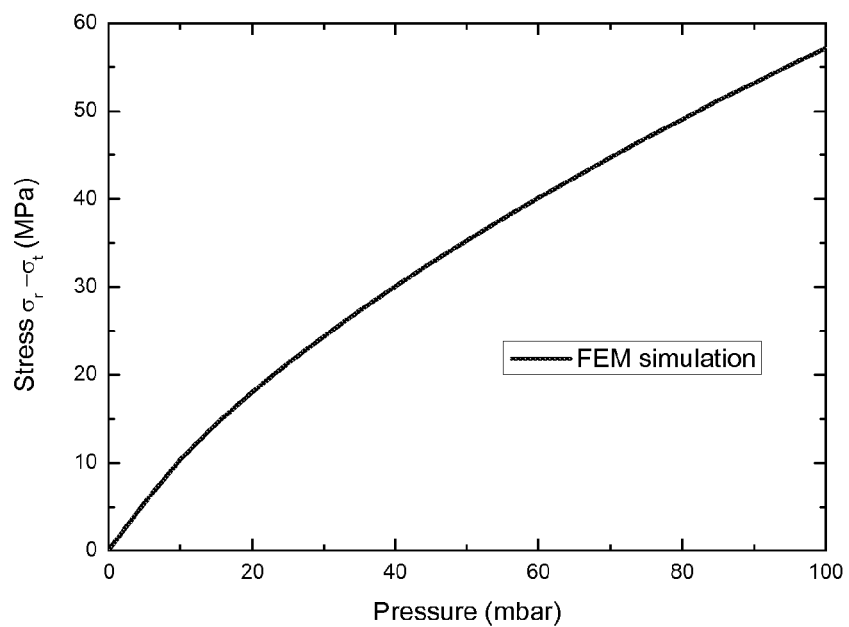
FIG. 18 shows a FEM simulation of the evolution of the bending stress with pressure.

The evolution of this stress with the pressure at R=7.35 mm is illustrated in FIG. 18.

Figure 19:
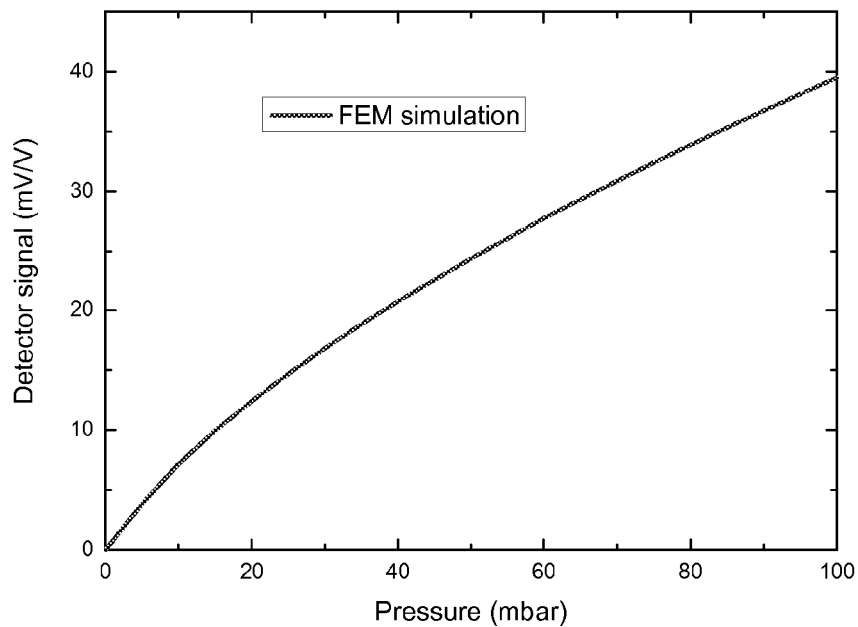
FIG. 19 shows a FEM simulation of the detector signal v. pressure.

The detector signal per volt of bias is shown in FIG. 19.

Figure 20:
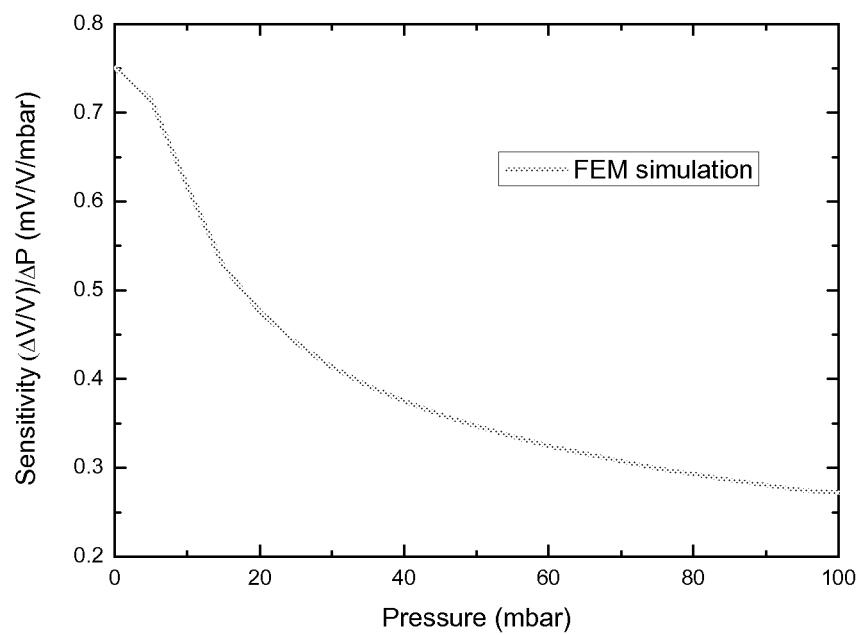
FIG. 20 illustrates the sensitivity of the sensor per mbar of pressure and per volt of bias.

It is also useful to give the sensitivity of the sensor per mbar of pressure and per volt of bias is illustrated in FIG. 20.

At 20 mbar the sensitivity is about S=0.5 mV/V/mbar

For a bias of 2V we have simply 1 mV per mbar.

The signal of the detector can be monitored without problem using simple operational amplifier.

A minimum resolution of 1 mbar is expected for this integrated pressure sensor.

Figure 21:
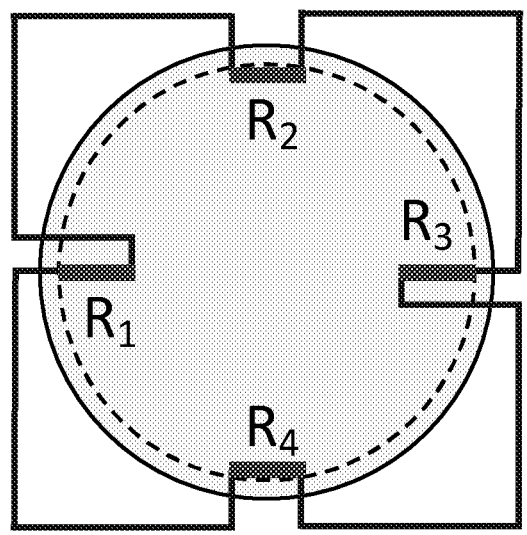
FIG. 21 illustrates another embodiment of a pressure sensor.

It could be needed to shift partly the interconnections outside of the fluidic pathway (resistors R1-R4 not to scale) as illustrated in FIG. 21.

The interconnections that are not in contact with the liquid could be either metallized or made by increasing the dose of the p+ layer since we do not have any limitation in the region not covered by the n+ layer.

The electrical insulation of the interconnections and the resistors can be obtained via an additional non-conductive layer. This new layer should be considered for the design of the detector (increase of the membrane stiffness . . . ).

As one will readily understand from this description and from the illustrative non-limiting examples, the regulator according to the invention can be used in different applications and in different ways and the different embodiments relating to different applications can be combined together if desired.

In addition, since the system according to the invention may be sensitive to particles which can form a channel obstruction, the device should therefore preferably include:
⇒ A filter at the inlet
⇒ A hydrophilic coating of the rod and the cylinder to prevent protein binding (eg PEG . . . )

The sensitivity to particles should be considered during the cleaning of the different parts and the assembly of the device in clean room.

Many additional features can be implemented and its field of utilization can be extended to other applications than hydrocephalus treatment or drug delivery requiring the same principle of functioning.

Of course, other dimensions may be envisaged for other applications of the device and all embodiments are given as illustrative examples that should not be construed in a limiting manner.

As mentioned above, the description of the present invention has been made in the frame of drug delivery and hydrocephalus shunt to drain CSF but is it not limited to this specific application and other applications may be envisaged, in the medical or in other fields. The possibility to integrate a pressure sensor into the silicon membrane is a major advantage since the physicist can monitor the CSF pressure externally using a wireless system. The device is passive and anti-siphoning thanks to its particular flow vs. pressure characteristics. No ageing is expected. The device can be tested at the wafer level using gas flow meter. All materials in contact with the CSF are bio-compatible.

As one will understand from the previous description, the regulator may be used as check valve (FIG. 14). It may also be used as a valve that closes at high pressure (when the holes are closed because the membrane is fully deformed), for example when the pressure reaches a predetermined high value or alternatively, in a variant, one may ensure that the regulator is open even at high pressure, i.e. when the pressure reached a predetermined high value. To this effect, it is necessary to place at least one hole close to the side of the cavity 6, thus ensuring that even when the membrane is fully deformed, this hole will not be closed (as the others). As one understands, the characteristics of the regulator may be influenced by the position of the holes and their number.

In the medical field, the device may be implanted or not and may be made of biocompatible materials, if necessary. Of course, according to circumstances, other materials might be envisaged. Also other values are possible, depending on the application, and the examples given herein are purely illustrative and non limitative.

Also, the sizes and shapes of the regulator and of the devices may be varied as wished by the skilled man depending on the application and the desired effects.

For instance, the cavities on both sides of the membrane (see FIGS. 4a, 4b and 14) may be identical or different in size and shape.

In addition, the threshold pressure values (first, second, predetermined high value) can be chosen or determined by a skilled man depending on the application and/or use of the regulator.

The materials used can be of any type suitable for the intended use of the regulator. They are biocompatible in case of an implantable device. They may undergo specific treatments and may also be coated with agents, for example hydrophilic agents.

The invention claimed is:

1. Fluid flow regulator (1) of the passive type having a fluid inlet adapted to be connected to a fluid reservoir and a fluid outlet (13) adapted to be connected to a delivery location, said regulator comprising a rigid substrate (2) and a resilient membrane (3) tightly linked together in predefined linking areas (4) so as to define a cavity (6) therebetween, said cavity (6) being connected to said fluid outlet (13) while said membrane (3) has a first surface (12) opposite said cavity (6) which is connected to said fluid inlet, said membrane (3) having a through hole (15) contiguous with said cavity (6), to define a pathway for a fluid from said fluid inlet to said fluid outlet (13), and being flexible so as to be able to come into contact with said substrate (2), within said cavity (6) and with a portion including said through hole (15), in case a fluid applies a pressure on said first surface (12) that is larger than a first predefined threshold value, which results in hindering a fluid from flowing through said through hole (15), wherein said membrane (2) comprises at least one additional through hole (15) contiguous with said cavity (6) and arranged such that a fluid may flow through it in case said fluid applies a pressure on said first surface (12) that is larger than said first predefined threshold value but smaller than a second predefined threshold value, said membrane (3) and said additional through hole (15) being further arranged so that a fluid flow rate is be substantially linear as a function of the pressure applied on said first surface (12) in a range going approximately from said first to said second predefined threshold values.

2. Regulator (1) according to claim 1, wherein said membrane (3) comprises n additional through holes (15) contiguous with said cavity (6), each j-th additional through hole being arranged such that a fluid may flow through it in case said fluid applies a pressure on said first surface (12) that is larger than a j-th predefined threshold value but smaller than a (j+1)-th predefined threshold value, said membrane and said n additional through holes being further arranged so that a fluid flow rate is substantially linear as a function of the pressure applied on said first surface in a range going approximately from said first to said (n+1)-th predefined threshold values.

3. Regulator (1) according to claim 2, wherein each of said through holes (15) is designed such that it has a fluidic resistance increasing linearly as a function of the pressure applied on said first surface (12) within a pressure range going approximately from said first predefined threshold value to its corresponding predefined upper threshold values, such that said fluid flow rate is substantially constant.

4. Regulator according to o claim 2, wherein said through holes (15) are arranged in series (602, 603, 604) and in that it comprises an occluding element (610, 710) arranged relative to said membrane (600, 700) so as to be movable between at least a first and a second positions, said occluding element presenting at least one opening (612, 712) and being designed so as to be able to occlude selectively at least one of said series in said first position and to let said series open in said second position by matching said opening with said series.

5. Regulator according to claim 4, wherein said occluding element is a thin film rotatable upon said membrane.

6. Regulator according to claim 4, wherein said occluding element (610, 710) is designed to be rotatable between at least two different positions to adjust any or any combination of the parameters within the group comprising: fluid flow rate, temperature, fluid viscosity or fluid nature.

7. Regulator (1) according to claim 1, wherein said through holes (15) have shapes without any sharp edge.

8. Regulator (1) according to claim 7, wherein each of said through holes (15) may have a shape such as circular, elliptical, oblong and elongated shapes.

9. Regulator (1) according to claim 1, wherein said through holes (15) are distributed over said membrane (3) along a spiral curve.

10. Regulator according to claim 1, wherein it comprises an additional rigid substrate (420, 520) tightly linked to said resilient membrane (401, 501) in predefined linking areas on the first surface side so as to define an additional cavity (406, 506) therebetween, each of the substrates having an inlet/outlet hole (421, 521) connected with the corresponding cavity.

11. Regulator according to claim 1, wherein both said substrate and said membrane exhibit a roughness in the range between 0.5 and 100 nm RMS, at least in said linking areas (4).

12. Regulator according to claim 1, wherein it comprises at least one pillar (803) in front of said through hole(s) (15) in said cavity (6).

13. Regulator according to claim 12, wherein it comprises at least an additional pillar(s) (808) on the other side of said hole(s) (15).

14. Regulator according to claim 13, wherein the additional pillar(s) (808) on the other side of said hole(s) (15) is in contact with the membrane to make a check-valve.

15. Regulator according to claim 1, wherein it comprises an anti-bonding layer on the membrane (3) and/or on the pillars (803, 808).

16. Regulator as defined in claim 1, wherein it closes when said pressure reaches a predetermined high value.

17. Regulator as defined in claim 1, wherein it remains open even when said pressure reaches a predetermined high value.

18. Regulator as defined in claim 1, wherein it comprises means to measure the deformation of the membrane.

19. Regulator as defined in claim 1, wherein it comprises a particle filter.

20. Regulator as defined in claim 1, wherein the parts in contact with the fluid are coated with hydrophilic agents.

21. Regulator as defined in claim 1, wherein the deformation sensor is powered and monitored by external means.

22. Process for the fabrication of a fluid flow regulator (1) according to claim 1, comprising the steps consisting in:
   a) providing a resilient membrane (3);
   b) applying a sacrificial layer on a first surface (12) of said resilient membrane;
   c) etching a plurality of holes in said membrane, said sacrificial layer defining a etch stop;
   d) applying an additional layer on said sacrificial layer;
   e) removing said sacrificial layer inside said holes;
   f) assembling said membrane with a rigid substrate (2) in predefined linking areas (4) of its side opposite to said first surface so as to define a cavity (6) therebetween;
   g) trimming said additional layer at predefined locations to finalise through holes (15) in the membrane.

23. Process according to claim 22, characterised in that steps e) and g) are carried out simultaneously.

24. Process according to claim 22, characterised in that said additional layer is a polymer layer which is applied by spraying, spinning or lamination.

25. Process according to claim 22, wherein the substrate is etched so as to create pillars and outlet hole.

26. Drug infusion device comprising a drug reservoir connected to a fluid flow regulator (1) according to claim 1 as well as infusion means for delivering a drug into a patient's body.

27. A hydrocephalus auto-regulated valve comprising at least a regulator as defined in claim 1.

\* \* \* \* \*